United States Patent [19]

Kida et al.

[11] 4,343,959
[45] Aug. 10, 1982

[54] PROCESS FOR THE PRODUCTION OF TERTIARY OLEFIN

[75] Inventors: Koichi Kida, Toyosaka; Yoshio Kawai, Niigata; Yutaka Tamura, Niigata; Yoshiharu Suzuki, Niigata, all of Japan

[73] Assignee: Mitsubishi Gas Chemical Co., Inc., Tokyo, Japan

[21] Appl. No.: 280,071

[22] Filed: Jul. 2, 1981

[30] Foreign Application Priority Data

Jul. 25, 1980 [JP] Japan .................. 55/102074

[51] Int. Cl.³ .................. C07C 1/20; C07C 11/08
[52] U.S. Cl. .................. 585/640
[58] Field of Search .................. 585/640

[56] References Cited

U.S. PATENT DOCUMENTS

3,170,000  2/1965  Verdol .................. 585/640
4,065,507 12/1977  Hardman et al. .................. 562/538
4,254,296  3/1981  Manara et al. .................. 585/640

FOREIGN PATENT DOCUMENTS

2534544  2/1976  Fed. Rep. of Germany .

OTHER PUBLICATIONS

Chem. Abs. 59, 11232f (1963).
Chem. Abs. 92, 170022(a) 1980.
Derwent, 15070W/09 JH 909H-602.
Derwent, 01935C/02 DT 2924-869.

*Primary Examiner*—Curtis R. Davis
*Attorney, Agent, or Firm*—Wyatt, Gerber, Shoup, Scobey & Badie

[57] ABSTRACT

A tertiary olefin is produced by making a gaseous tertiary ether usually represented by the following general formula:

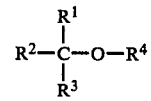

wherein $R^1$, $R^2$ and $R^3$ are alkyl groups each having 1–4 carbon atoms which may be same or different each other and $R^4$ is an alkyl group having 1–3 carbon atoms, contact a catalyst obtained by calcining a silica-alumina compound at 700°–1100° C. in order to carry out cracking of the tertiary ether.

11 Claims, No Drawings

PROCESS FOR THE PRODUCTION OF TERTIARY OLEFIN

The present invention relates to a process for the production of a corresponding tertiary olefin from a tertiary ether (sometimes referred to "TE" hereinafter). More particularly, it relates to a process for the production of a corresponding tertiary olefin from a tertiary ether in high purity and at high yield using a novel catalyst.

In recent years, the production of methyl-tert-butyl ether (hereafter referred to as MTBE) has been actively carried out in Europe and U.S.A. in order to use it as an octane booster for gasoline. Also in Japan, there is shown a strong tendency to produce MTBE and there is a possibility to get it at a price nearly equal to that of gasoline in the near future. At that time, this process for the production of isobutylene obtained by the cracking of this MTBE is expected to be overwhelmingly at advantage over conventional sulfuric acid extraction process using $C_4$ fraction. As one of prior conditions, it is necessary that the cracking reaction of MTBE proceeds at high conversion (high cracking ratio) and high selectivity and, further, it is desirable that isobutylene and methanol which are produced by cracking have sufficiently high purities as industrial raw materials, respectively.

A tertiary olefin having a high purity is a useful material in industries; for instance, isobutylene having a high purity is expected to be used as the raw material for butylene rubber, MMA and the like.

The cracking of MTBE can be conducted in liquid phase at a temperature not higher than 150° C. in the presence of an acid in accordance with the following equilibrium reaction:

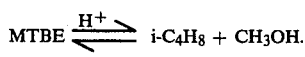

However, in order to make this reaction proceed advantageously, it is appropriate to carry out the catalytic reaction in vapor phase at a temperature not lower than 180° C. and there is found a description in, for instance, "Chemical abstracts" 59. 11231f (1963), that this reaction is carried out on the surface of activated alumina at a temperature of 175°–380° C. under normal pressure. Then, in U.S. Pat. No. 3,170,000, it is described that satisfactory results were obtained by the preparation of a solid catalyst such as alumina or magnesia having a low specific surface area. However, in this case, the reaction should be carried out at high temperatures because of the low activity of the catalyst. None the less, the conversion is not higher than 70% resulting in the necessity to recover MTBE which is not altered. Though this MTBE can usually be recovered by distillation, mixing of methanol with MTBE recovered can not be avoided in this case resulting in promotion of the by-product of dimethyl ether and difficulty in separating it from isobutylene. In order to minimize the amount of MTBE which is not altered, it is necessary to raise up the one-pass conversion. For this purpose, the temperature is further raised up and the time to contact catalyst is extended; none the less, there is seen a tendency that dimethyl ether is easily produced as a by-product. Consequently, the production of by-product dimethyl ether can not be avoided in both cases.

DEOS No. 2534544 discloses cracking of a tertiary ether in the presence of a catalyst of an activated alumina which is modified by the reaction with an organosilicon compound. However, in this process, though the selectivity was improved by carrying out the cracking of MTBE at a low temperature and thereby reducing the conversion of MTBE, the production of by-product dimethyl ether was, on the other hand, increased when the conversion was increased; consequently, it was impossible to increase both of conversion and selectivity. Also the use of expensive organosilicon compound causes a burden for the catalyst cost.

Also in DEOS No. 2924869, there was obtained a result that the cracking reaction proceeds almost quantitatively by using a catalyst consisting of silica as the main component and various metal oxides, particularly 0.2% of alumina as the metal oxide. However, silica itself has no catalytic activity when it is used alone. When alumina was combined with silica, the cracking of MTBE was, according to the follow-up test conducted by the present inventors, conducted actively; however, also the polymerization activity of isobutylene was remarkable and the activity decreased in a short time; thus, no satisfactory result was obtained. Even though it is assumed that a catalyst like that in said process having a very low concentration of alumina shows an appropriate activity for cracking in the narrow range of from no activity to high activity, it is practically difficult to obtain a catalyst which gives a satisfactory result at a high reproducibility, and the industrial use of such a catalyst is considered to be impossible.

Further, in Derwent (CPI) 15070W/09 j49094-602, highly excellent results are obtained when the cracking of MTBE is conducted by using an activated carbon catalyst. However, according to the follow-up test conducted by the present inventors, when the activated carbon catalyst is used, there takes place a phenomenon that carbon which seems to be produced from olefin in reaction products deposits and there is found a defect that the operation for reactivation of the activated carbon catalyst used to remove the carbon deposited with oxygen can not be conducted because the catalyst activated carbon burns out together with the carbon deposited. Thus, it was found that the catalyst has to be frequently exchanged with new one.

As mentioned above, in case wherein conventional processes are used, even though the conversion of tertiary ether or the selectivities of tertiary olefin and primary alcohol are satisfactory in outline, there are defects such as no possibility to increase both of conversion and selectivity, low reproducibility depending upon catalyst, high cost of catalyst, complexity to prepare catalyst, short life of catalyst and difficulty to regenerate catalyst. Consequently, these processes are not suitable for practical uses.

The present inventors have been eagerly studying to eliminate those defects in the conventional processes and find out a catalyst which has high cracking activity and high selectivity, high reproducibility as practical catalyst, low cost, long life and high stability and have succeeded in developing the present invention.

That is, the present inventors have found that a catalyst which is highly suitable to the present reaction can be provided by calcining ordinary silica-alumina under specific conditions.

In a process to produce a tertiary olefin from a tertiary ether as the raw material, the present invention provides a process to produce a tertiary olefin which comprises making a gaseous tertiary ether into contact with a catalyst obtained by calcining a silica-alumina compound at 700°–1100° C.

Silica-alumina compounds used in the present invention include those which are, for example, natural silica-alumina compounds such as acidic clay and activated clay which contain silica-alumina and other impurities, synthetic silica-alumina compounds obtained, for instance, by making an aluminum component deposit on the surface of a silica hydrogel and the like. They may be also silica-alumina compounds on the market used for the catalysts for other reactions. The third component other than silica-alumina may be contained; however, at least silica and alumina have to be inevitably contained. In general there has been used a silica-alumina compound wherein silica is 2–98 wt.% and alumina is 98–2 wt.% to the total amount of silica and alumina.

In addition, each of these silica-alumina compounds has an acidic point before and even after calcination.

These silica-alumina compounds are calcined at 700°–1100° C., preferably 750°–1000° C. When the calcination temperature is lower than 700° C., the activity to cause side-reactions such as polymerization or dehydration can not be suppressed; however, when the calcination temperature exceeds 1100° C., the cracking activity is remarkably lowered and a satisfactory conversion of TE cannot be obtained at higher reaction temperatures as well as lower reaction temperatures.

Though the calcination time may be 0.5–50 hours, preferably 2–24 hours, it may be appropriately selected in accordance with the calcination temperature and catalyst composition. When a silica-alumina compound has a high silica content, it is preferable to somewhat lower the calcination temperature or shorten the calcination time. When the alumina content is high, the calcination time gives little effect in this range of calcination temperature. Though the calcination is conducted in an atmosphere which contains an inert gas such as air, nitrogen, steam or a mixture of them, it is practically most desirable that the calcination is conducted in air.

There is no particular limitation on the calcination apparatus and any apparatus conventionally used can be used; that is, a stationary type one, for example, a muffle furnace, a gas-passing form one wherein, for example, quartz tubes are used in a cylindrical electric furnace and the like.

It is desirable that uniform calcination is carried out at a constant temperature as far as possible.

The catalyst of the present invention thus obtained has a specific surface area of about 30–150 m²/g and the physical performance thereof is so high that it can satisfactorily endure practical uses showing no physical change during the operation for a long time.

Though the catalyst prepared according to the present invention has a long life, the activity gradually decreases owing to the deposit of a slight amount of polymers thereto during its use for a long time. In such a case the activity can be easily recovered by blowing hot air having a temperature not lower than 500° C. and burning the material deposited thereto. Moreover, even if this operation for regeneration is carried out for a long time or repeated several times, the catalyst reveals no deterioration in mechanical strength.

Tertiary ethers used in the present invention may be any one conventionally used; in general, there can be used tertiary ethers represented by the following general formula:

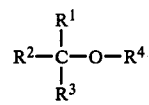

wherein $R^1$, $R^2$ and $R^3$ are alkyl groups each having 1–4 carbon atoms which may be same or different each other, preferably alkyl groups having 1–3 carbon atoms such as, for example, methyl group, ethyl group and isopropyl group and $R^4$ is an alkyl group having 1–3 carbon atoms, preferably methyl group or ethyl group, especially preferably methyl group.

Typical examples of tertiary ethers represented by said general formula and tertiary olefins obtained therefrom are illustrated below.

| Tertiary ether | Tertiary olefin |
|---|---|
| $H_3C-\underset{\underset{CH_3}{\vert}}{\overset{\overset{CH_3}{\vert}}{C}}-O-CH_3$ | $\underset{CH_3}{\overset{CH_3}{\diagdown}}C=CH_2$ |
| MTBE | isobutylene |
| $H_3C-\underset{\underset{CH_3}{\vert}}{\overset{\overset{CH_3}{\vert}}{C}}-O-C_2H_5$ | $\underset{CH_3}{\overset{CH_3}{\diagdown}}C=CH_2$ |
| ethyl-tert-butyl ether | isobutylene |
| $CH_3-CH_2-\underset{\underset{CH_3}{\vert}}{\overset{\overset{CH_3}{\vert}}{C}}-O-CH_3$ | $CH_3-\overset{\overset{CH_3}{\vert}}{C}=CH-CH_3$ 2-methyl-2-butene |
| methyl-tert-amyl ether | $CH_2=\overset{\overset{CH_3}{\vert}}{C}-CH_2-CH_3$ 2-methyl-1-butene |
| $\underset{\underset{CH_3}{\vert}}{\overset{\overset{CH_3-\overset{\overset{CH_3}{\vert}}{C}-H}{\vert}}{CH_3-C-O-CH_3}}$ | $CH_3-\overset{\overset{CH_3}{\vert}}{C}=\overset{\overset{CH_3}{\vert}}{C}-CH_3$ 2,3-dimethyl-2-butene $CH_2=\overset{\overset{CH_3}{\vert}}{C}-\overset{\overset{CH_3}{\vert}}{CH}-CH_3$ |
| 2,3-dimethyl-2-methoxybutane | 2,3-dimethyl-1-butene |
| $CH_3-\underset{\underset{\underset{\underset{CH_3}{\vert}}{CH_2}}{\underset{CH_2}{\vert}}}{\overset{\overset{CH_3}{\vert}}{C}}-O-CH_3$ | $CH_2=\overset{\overset{CH_3}{\vert}}{C}-CH_2-CH_2-CH_3$ 2-methyl-1-pentene $CH_3-\overset{\overset{CH_3}{\vert}}{C}=CH-CH_2-CH_3$ |
| 2-methoxy-2-methylpentane | 2-methyl-2-pentene |

| Tertiary ether | Tertiary olefin |
|---|---|
| CH₃—C(CH₃)(OCH₃)—CH₂—CH₃ ... CH₂=C(CH₂CH₃)—CH₂—CH₃ (2-ethyl-1-butene) and CH₃—CH=C(CH₃)—CH₂—CH₃ | |
| 3-methoxy-3-methylpentane | 3-methyl-2-pentene (cis- and trans-) |

Among them, MTBE, methyl-tert-amyl ether and ethyl-tert-butyl ether are the most desirable for industrial raw material.

These tertiary ethers may be ones obtained by any production process. For instance, in the case of MTBE, one obtained from isobutylene having a high purity and methanol having a high purity can be used; however, it is preferable to use $C_4$ fraction containing isobutylene and methanol, and such a use has an important meaning in industries that is, it corresponds to extraction of isobutylene from $C_4$ fraction containing isobutylene.

The temperature of cracking reaction is 120°–350° C., preferably 170°–300° C. The reaction pressure may be any level under which the tertiary ether is in gaseous state at said temperature condition; usually it is desirable to carry out the operation under 0–10 kg/cm² (gauge). Though there is a tendency that the reaction pressure is lower as the conversion of TE is higher a sufficiently high conversion can be attained even under a pressure of 5–6 kg/cm² (gauge) which is suitable for the fractional distillation of tertiary olefin produced. The supplying velocity of tertiary ether per unit volume of catalyst (WHSV, g/cc/hr) is 0.3–100 g/cc/hr, preferably 0.5–10 g/cc/hr.

The present invention has advantages that both of the conversion of tertiary ether and the selectivities of tertiary olefin and primary alcohol, respectively, can be increased with high reproducibility, the catalyst has a low cost and, in addition, the preparation and the regeneration thereof are easy. Thus, the present invention is highly valuable in industries.

The embodiment of the present invention will be elucidated with following examples.

EXAMPLES 1–5 AND COMPARATIVE EXAMPLE 1

A drying agent on the market Neobead D ($Al_2O_3$: 90 wt.%, $SiO_2$: 10 wt.%; manufactured by Mizusawa Industrial Chemicals, Ltd.) was ground to particles having a size of 10–30 meshes and they were calcined under the conditions shown in Table 1. Then 20 cc of the product was charged in a reaction column made of stainless steel having an inside diameter of 16 mm$\phi$ and a length of 50 cm and the cracking reaction of MTBE was conducted. The calcination conditions, reaction conditions and the results obtained are shown in Table 1.

TABLE 1

| Number of Example | 1 | 2 | 3 | 4[*1] | 5 | Comp. 1 |
|---|---|---|---|---|---|---|
| Catalyst[*2] | | | | | | |
| Calcination temperature (°C.) | 800 | 1000 | 1000 | 1000 | 1000 | 600 |
| Calcination time (hrs) | 6 | 6 | 24 | 24 | 6 | 6 |
| Reaction conditions | | | | | | |
| Reaction pressure (kg/cm² gauge) | 5 | 5 | 5 | 5 | 2 | 5 |
| Preheating temperature (°C.) | 200 | 200 | 200 | 250 | 180 | 200 |
| Reaction temperature (°C.) | 200 | 200 | 200 | 250 | 180 | 200 |
| WHSV (g/cc/hr) | 2 | 2 | 2 | 4 | 2 | 2 |
| Results | | | | | | |
| Conversion of MTBE (%) | 96.8 | 96.7 | 95.2 | 98.1 | 85.2 | 76.5 |
| Selectivity of isobutylene (mol %) | 99.9 | 100 | 100 | 99.8 | 100 | 98.7 |
| Selectivity of methanol (mol %) | 96.4 | 97.5 | 98.5 | 98.3 | 99.5 | 93.5 |
| Selectivity of dimethyl ether (mol %) | 3.6 | 2.5 | 1.5 | 1.7 | 0.5 | 6.5 |
| Selectivty of diisobutylene (mol %) | Trace | — | — | 0.2 | 0.0 | 1.3 |

Notes:
[*1]The reaction was continued for 100 hours; however, the results of reaction showed no substantial deterioration.
[*2]The calcination was conducted by gas-passing form using a quartz tube in a cylindrical electric furnace.

EXAMPLES 6–10 AND COMPARATIVE EXAMPLES 2 AND 3

A silica-alumina catalyst N-631 L on the market ($Al_2O_3$: 13%, $SiO_2$: 87%; manufactured by NIKKI CHEMICAL CO., LTD.) was ground to particles having a size of 10–30 meshes and they were calcined under the conditions shown in Table 2. Using each of these catalysts, the reaction was conducted according to the procedure same as that in Examples 1–5. The calcination conditions, reaction conditions and the results obtained are shown in Table 2.

TABLE 2

| Number of example | 6 | 7 | 8 | 9[*2] | 10 | Comp. 2 | Comp. 3 |
|---|---|---|---|---|---|---|---|
| Catalyst[*1] | | | | | | | |
| Calcination temperature (°C.) | 1000 | 1000 | 1000 | Regenerated at 500° C. | 1000 | 600 | 600 |
| Calcination time (hrs.) | 6 | 6 | 24 | | 24 | 6 | 6 |
| Reaction conditions | | | | | | | |
| Reaction pressure (kg/cm² gauge) | 5 | 5 | 5 | 5 | 10 | 5 | 5 |
| Preheating temperature (°C.) | 240 | 200 | 250 | 250 | 200 | 200 | 170 |
| Reaction temperature (°C.) | 240 | 200 | 250 | 250 | 280 | 200 | 170 |
| WHSV (g/cc/hr) | 3.0 | 3.0 | 2.5 | 2.5 | 8.0 | 3.0 | 2.0 |
| Results | | | | | | | |
| Conversion of MTBE (%) | 99.0 | 96.2 | 99.5 | 99.3 | 97.5 | 98.0[*3] | 91.4[*4] |
| Selectivity of isobutylene (mol %) | 99.8 | 99.9 | 99.6 | 99.7 | 99.3 | 37.3 | 76.8 |

TABLE 2-continued

| Number of example | 6 | 7 | 8 | 9*2 | 10 | Comp. 2 | Comp. 3 |
|---|---|---|---|---|---|---|---|
| Selectivity of methanol (mol %) | 98.8 | 99.6 | 99.0 | 99.1 | 99.2 | 86.5 | 96.9 |
| Selectivity of dimethyl ether (mol %) | 1.2 | 0.4 | 1.0 | 0.9 | 0.8 | 13.5 | 3.0 |
| Selectivity of diisobutylene (mol %) | 0.2 | 0.1 | 0.4 | 0.3 | 0.7 | 36.5 | 15.8 |

Notes:

*[1] The calcination was conducted according to gas-passing form by allowing air to pass through a quartz column having an inside diameter of 20 mmφ at a rate of 5 l/hr.

*[2] Using the catalyst same as that in Example 8, the reaction was continued for 50 hours. Then the conversion of MTBE decreased to 97%. Accordingly, regeneration was carried out by allowing air having a temperature of 500° C. to pass at a rate of 2 l/hr for 2 hours and it was used for the reaction in Example 9 after confirmation of no generation of $CO_2$.

*[3] The conversion decreased to 90% after 10 hours elapsed.

*[4] The conversion decreased to 80% after 17 hours elapsed.

EXAMPLES 11-13 AND COMPARATIVE EXAMPLES 4-7

A water glass solution ($SiO_2$: 4.7%) and carbon dioxide were allowed to react to obtain a slurry of silica hydrogel. After aging it, a predetermined amount of aqueous alumina solution ($Al_2O_3$: 7.3%) was added thereto to make alumina deposit on silica hydrogel. After further aging thereof, ammonia water was added thereto adjust pH to 8.0. Then the product was filtered, washed to remove ammonia and ground to particles having a size of 10-30 meshes and they were calcined at 600° C. in a quartz column for 24 hours while allowing air to pass through it. Thus there were obtained a silica-alumina compound A and a silica-alumina compound B, respectively. The composition of both compounds were as follows:

|  | $Al_2O_3$ | $SiO_2$ |
|---|---|---|
| Silica-alumina compound A | 25% | 75% |
| Silica-alumina compound B | 2% | 98% |

These silica-alumina compounds were further calcined and used for the cracking reaction according to the procedure same as that in Examples 1-5. The calcination conditions, reaction conditions and the results are shown in Table 3.

TABLE 3

|  | Silica-alumina compound A | | | Silica-alumina compound B | | | |
|---|---|---|---|---|---|---|---|
| Number of example | 11 | Comp. 4 | Comp. 5 | 12 | 13 | Comp. 6 | Comp. 7 |
| Catalyst*[1] | | | | | | | |
| Calcination temperature (°C.) | 800 | 1200 | 600 | 800 | 700 | 600 | 1200 |
| Calcination time (hrs.) | 6 | 6 | 24 | 1 | 6 | 24 | 24 |
| Reaction conditions | | | | | | | |
| Reaction pressure (kg/cm² gauge) | 5 | 5 | 5 | 5 | 5 | 5 | 5 |
| Reaction temperature (°C.) | 200 | 250 | 200 | 200 | 200 | 200 | 250 |
| WHSV (g/cc/hr) | 2 | 2 | 2 | 2 | 2 | 2 | 2 |
| Results of reactions | | | | | | | |
| Conversion of MTBE (%) | 97.2 | 21.2 | 98.1 | 97.0 | 97.5 | 96.3 | no reaction occurred |
| Selectivity of isobutylene (mol %) | 99.4 | 100 | 44.2 | 96.1 | 95.7 | 56.0 | no reaction occurred |
| Selectivity of methanol (mol %) | 98.7 | 91 | 89.1 | 99.0 | 98.4 | 89.6 | no reaction occurred |
| Selectivity of di-methyl ether (mol %) | 1.3 | 9 | 10.9 | 1.0 | 1.6 | 10.4 | no reaction occurred |
| Selectivity of di-isobutylene (mol %) | 0.6 | 0 | 30.5 | 3.9 | 4.3 | 20.4 | no reaction occurred |

Note:
*[1] Calcination was conducted in a stationary form using a muffle furnace.

EXAMPLE 14

Using the catalyst obtained according to the procedure same as that in Example 8, the cracking of methyl-tert-amyl ether was conducted. Reaction conditions and results are shown in Table 4.

TABLE 4

| Reaction conditions | |
|---|---|
| Reaction pressure (kg/cm² gauge) | 5 |
| Preheating temperature (°C.) | 200 |
| Reaction temperature (°C.) | 200 |
| WHSV (g/cc/hr) | 3 |
| Results | |
| Conversion of methyl-tert-amyl ether (%) | 98.9 |
| Selectivity of tertiary olefin (mol %) | 99.2 |
| Selectivity of methanol (mol %) | 99.1 |
| Selectivity of dimethyl ether (mol %) | 0.9 |
| Selectivity of olefindimer (mol %) | 0.8 |

EXAMPLE 15

Using the catalyst obtained according to the procedure same as that in Example 7, the cracking of ethyltert-butyl ether was conducted. Reaction conditions and results are shown in Table 5.

TABLE 5

| Reaction conditions | |
|---|---|
| Reaction pressure (kg/cm² gauge) | 5 |
| Preheating temperature (°C.) | 250 |
| Reaction temperature (°C.) | 250 |
| WHSV (g/cc/hr) | 4 |
| Results | |
| Conversion of ethyl-tert-butyl ether (%) | 99.3 |
| Selectivity of isobutylene (mol %) | 99.7 |
| Selectivity of ethanol (mol %) | 99.2 |
| Selectivity of diethyl ether (mol %) | 0.8 |
| Selectivity of diisobutylene (mol %) | 0.3 |

We claim:

1. In a process to produce a corresponding tertiary olefin from a tertiary ether as the raw material, a process to produce a tertiary olefin which comprises making a gaseous tertiary ether contact a catalyst obtained by calcining a silica-alumina compound at 700°–1100° C. in order to carry out cracking of the tertiary ether.

2. The process as claimed in claim 1 wherein the ratios of silica and alumina to the total amount of silica and alumina are 2–98 wt.% and 98–2 wt.%, respectively.

3. The process as claimed in claim 1 wherein the calcination temperature of silica-alumina compound is 750°–1000° C.

4. The process as claimed in claim 1 wherein the calcination time of silica-alumina compound is 0.5–50 hours.

5. The process as claimed in claim 1 wherein a catalyst having a specific surface area of 30–150 m²/g after calcination is used.

6. The process as claimed in claim 1 wherein tertiary ethers represented by the following general formula:

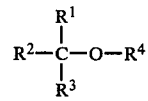

wherein $R^1$, $R^2$ and $R^3$ are alkyl groups each having 1–4 carbon atoms which may be same or different each other and $R^4$ is an alkyl group having 1–3 carbon atoms are used as the raw material.

7. The process as claimed in claim 1 or 6 wherein methyl-tert-butyl ether, ethyl-tert-butyl ether, methyl-tert-amyl ether, 2,3-dimethyl-2-methoxybutane, 2-methoxy-2-methylpentane or 3-methoxy-3-methylpentane is used as the raw material.

8. The process as claimed in claim 1 wherein the reaction temperature at which a tertiary olefin is produced from the corresponding tertiary ether is 120°–350° C.

9. The process as claimed in claim 1 wherein the reaction temperature at which a tertiary olefin is produced from the corresponding tertiary ether is 170°–300° C.

10. The process as claimed in claim 1 wherein the supplying velocity of tertiary ether per unit volume of catalyst (WHSV) is 0.3–100 g/cc/hr.

11. The process as claimed in claim 1 wherein the supplying velocity of tertiary ether per unit volume of catalyst (WHSV) is 0.5–10 g/cc/hr.

* * * * *